United States Patent [19]

Ferek-Petric

[11] Patent Number: 5,076,272
[45] Date of Patent: Dec. 31, 1991

[54] AUTOCONTROLLABLE PACEMAKER WITH ALARM

[75] Inventor: Bozidar Ferek-Petric, Zagreb, Yugoslavia

[73] Assignee: Telectronics Pacing Systems, Inc., Englewood, Colo.

[21] Appl. No.: 538,855

[22] Filed: Jun. 15, 1990

[51] Int. Cl.⁵ .............................................. A61N 1/362
[52] U.S. Cl. ............................................ 128/419 PG
[58] Field of Search .................. 128/419 PG, 419 PS

[56] References Cited

U.S. PATENT DOCUMENTS

| | | | |
|---|---|---|---|
| 3,713,449 | 1/1973 | Mulier | 128/419 P |
| 3,738,371 | 6/1973 | Raddi et al. | 128/419 PT |
| 3,842,844 | 10/1974 | Alferness | 128/422 |
| 4,140,131 | 2/1979 | Dutcher et al. | 128/419 PT |
| 4,203,448 | 5/1980 | Keller, Jr. | 128/419 PG |
| 4,345,603 | 8/1982 | Schulman | 128/419 PT |
| 4,481,950 | 11/1984 | Duggan | 128/419 PT |
| 4,488,555 | 12/1984 | Imran | 128/419 PT |
| 4,596,251 | 6/1986 | Plicchi et al. | 128/419 PG |
| 4,606,350 | 8/1986 | Frost | 128/419 PG |
| 4,884,576 | 12/1989 | Alt | 128/419 PG |

FOREIGN PATENT DOCUMENTS

1538/86  9/1986  Yugoslavia .

Primary Examiner—William E. Kamm
Assistant Examiner—Scott M. Getzow
Attorney, Agent, or Firm—Gottlieb, Rackman & Reisman

[57] ABSTRACT

An apparatus for administering electrotherapy, such as a pacemaker, having an alarm system including a relatively small alarm electrode affixed to the external surface of a non-conductive portion of the case of the apparatus, such as the neck. The apparatus, is implanted with the alarm electrode in contact with a muscle. A switch permits the alarm electrode to be used as the indifferent electrode for providing a patient alarm. The amplitude of the output may be varied to provide different alarm levels; i.e. different twitching intensity of the muscle, to permit the patient and physician to distinguish between alarms of diagnostic interest and those indicating a hazardous or emergency condition.

43 Claims, 8 Drawing Sheets

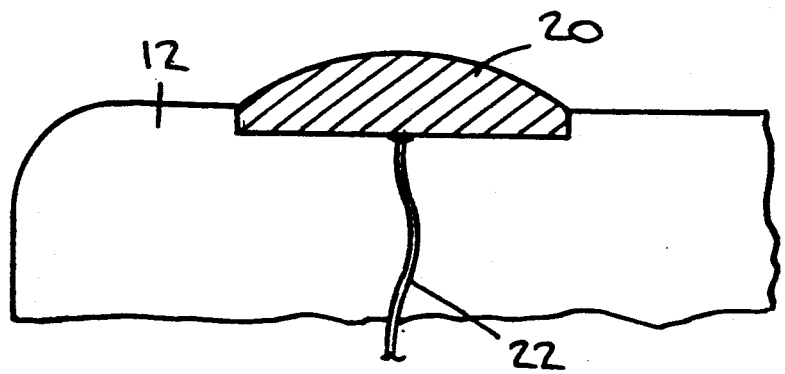
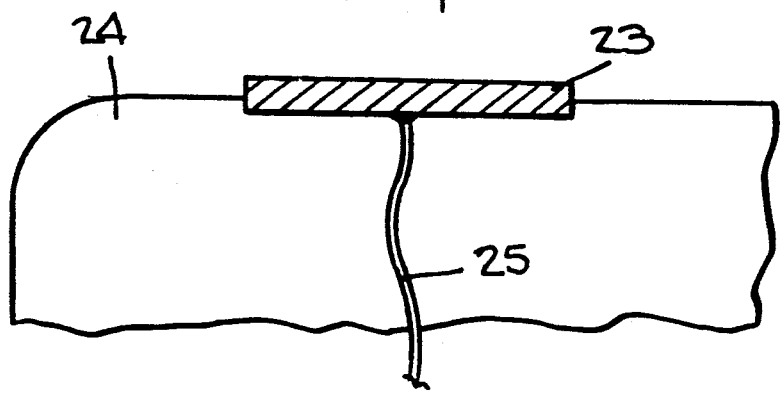
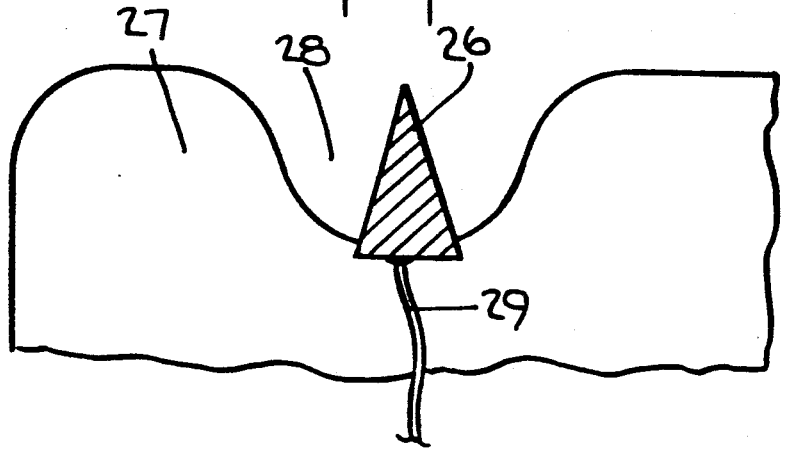

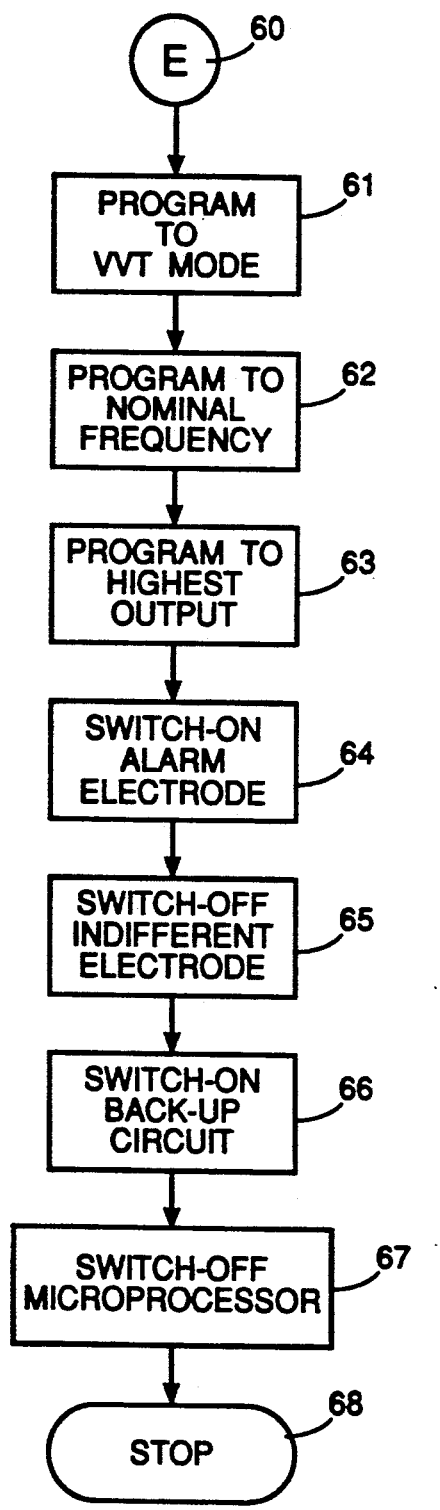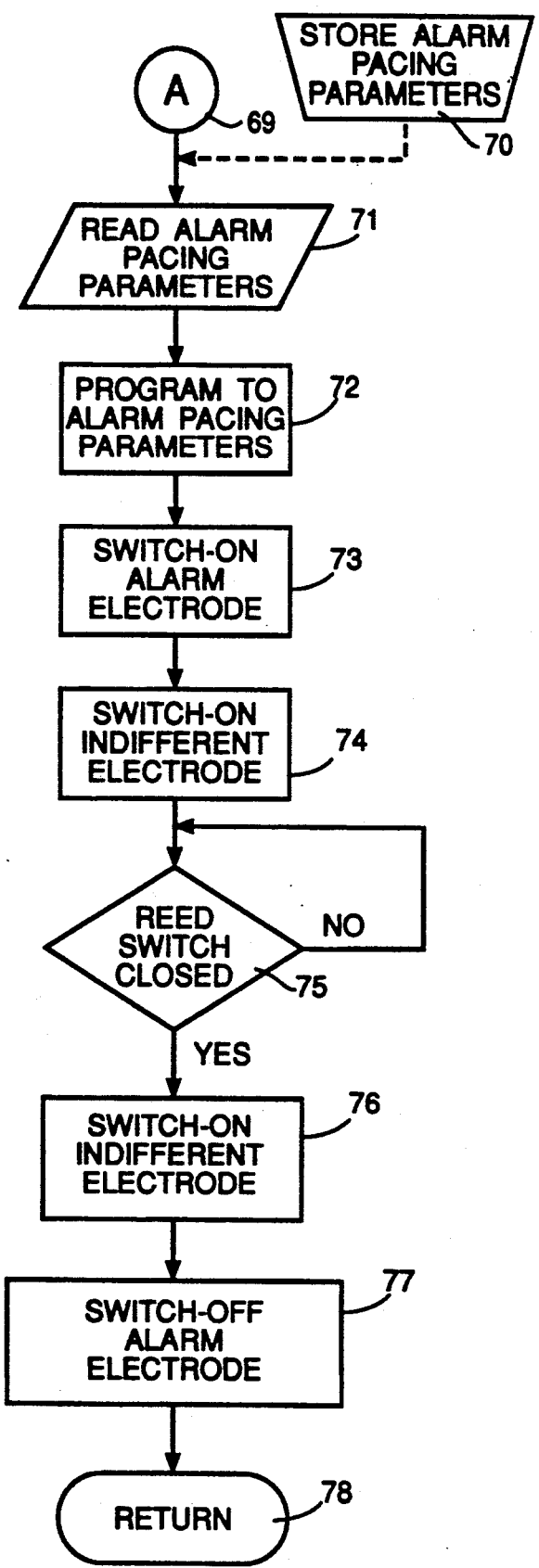
FIG. 5A.
FIG. 5B.

AUTOCONTROLLABLE PACEMAKER WITH ALARM

TECHNICAL FIELD

This invention relates to implantable cardiac electrotherapy apparatus, and to the follow-up of cardiac pacing and cardiac arrhythmias. More particularly, the invention pertains to apparatus having a patient alarm for warning about a pacing malfunction, a pacing system failure, or potentially hazardous cardiac arrhythmias.

BACKGROUND ART

Recent advances in pacemaker technology have rapidly introduced new clinical applications. The therapeutic benefit of pacing for all kinds of cardiac arrhythmias has been significantly increased by means of multiprogrammability and physiologic pacing.

Since a wide range of pacing parameters are programmable, pacemaker function can be closely tailored to the patient's needs in order to optimize the haemodynamic benefit. Pacing therapy has also been introduced for tachycardia control. Contemporary designs for implantable devices also include diagnostic features. Pacemaker patients come to follow-up sessions in a pacemaker center according to a prescribed individual schedule. An important purpose of these sessions is to either diagnose or to prevent the occurrence of events that are hazardous to the patient. A hazardous event can occur due to an impending pacing system failure, a cardiac pacing malfunction or disturbance, or a cardiac arrhythmia. Contemporary follow-up is based on accurate electrocardiologic and electronic measurements as well as on radiographic imaging.

The most frequent hazardous pacing system failure is battery depletion. While quite rare, lead fracture and insulation brakes may also occur. Various kinds of oversensing and undersensing phenomena are the most common pacing disturbances. The most hazardous pacing malfunction is loss of capture which may be the consequence of exit block, i.e. a rise in threshold above the programmed output. Lifethreatening arrhythmias can be triggered by premature ventricular contractions which are not always felt by the patient. Since pacemaker mediated tachycardia can also appear to be slow, the patient does not always feel this event. Many complications occur transiently, while certain physiologic and pathophysiologic conditions are sustained. Since all of the possible complications cannot be detected by the patient and his physician, it is possible for a problem to remain unidentified for extended periods of time.

During recent years of pacemaker design development, there have been many efforts to provide various detectors and indicators of pacing complications, in order to enhance safety by providing a warning to the patient and the physician.

Generally, the most efficient follow-up procedures utilize features incorporated into the pacemaker itself. Non-programmable pacemakers generally include only a magnet test function. The test frequency (of pacing) depends on the battery voltage, and decreases whenever the battery voltage decreases. There are also pacemakers, such as described in U.S. Pat. No. 3,842,844, which include electronic circuits which increase output pulse width as battery voltage decreases. There are programmable pacemakers which can be programmed after implantation by means of an external programmer. Pacemaker programming is a basic feature of patient follow-up. The underlying rhythm can be observed using low frequency programming. Overdrive of the spontaneous rhythm can be accomplished by increasing pacing frequency.

Since a rise of threshold precedes some pacing malfunctions, it is essential to determine the safety margin of the pacing output. As described in U.S. Pat. No. 3,713,449, the threshold can be measured by successive decreases of the output pulse width.

The pacing mode, the sensitivity, the refractory period and many other parameters can be programmed in multiprogrammable pacemakers. Precise programming within the optimal range of parameters can prevent many complications. Some complications can be intentionally provoked during a follow-up session by programming to particular combinations of parameters. This is especially significant in dual-chamber pacemakers.

A major advance in follow-up procedures was obtained by the introduction of telemetric pacemakers into clinical practice. Interrogation and telemetry readout are performed by using the programmer and provide many significant data values, such as, for example, values of the current program. If the pacemaker includes measurement functions, the telemetry readout can also provide values of the battery voltage, internal impedance of the battery, the measured lead impedance and the values of measured output parameters.

Recent pacemaker development is directed towards autoprogrammability. Many pacemakers include a backup mode of pacing which maintains stimulation in the event of significant battery depletion or microprocessor failure. Some pacemakers have an auto-capture function. The latter have electronic circuits for evoked response detection and the output is automatically increased whenever loss of capture is detected. If the threshold does not exceed the maximum output, the automatic output programming prevents complications caused by exit block. The newest dual-chamber and antitachycardia devices also include some important diagnostic features. Event counters memorize the number of premature ventricular contractions (PVCs) or the number of upper rate excesses. Bradycardia counters and interference counters are also used in follow-up. Antitachycardia pacemakers can provide a telemetry readout which indicates the number of tachycardia attacks, the number of successful and failed terminations, as well as the number of termination attempts.

Despite development in follow-up methods, patient safety depends largely on the follow-up interval schedule. In order to increase patient safety, many inventors have proposed electronic circuits for pacemakers which include special functions for patient control and warning. The basic clinical principle is to provide some signal to the patient whenever a pacing malfunction or a pacing system failure occurs.

One prior art example is an implantable device comprising an auxiliary battery which is switched on as a backup power supply whenever the primary power source is significantly depleted. An indication of switching is provided either by a variation of the pulse rate or by an additional set of electrodes remote from the heart. An acoustic signal has also been proposed for warning of impending battery depletion in pacemakers. A transducer or piezoelectric crystal for generating acoustic signals upon battery end-of-life detection is used. This type of design consumes additional energy for sound generation. Since sound is significantly attenuated within subcutaneous tissue, the efficiency of these systems is limited by the obesity of patients. Furthermore, slight deafness as well as the patient's ignorance of the signal cannot be excluded as important application considerations.

Instead of using acoustic signals, it is more convenient to provoke a non-hazardous symptom, easily recognizable by the patient. The most efficient alarm symptom is muscle twitching. It is actually a common complication of high output pacing in the unipolar mode. Since it does not affect pacing efficiency, it is not hazardous. However, pain tolerance is a psychological problem. A unipolar pacing system has an indifferent electrode (anode) on the pacemaker can. A bipolar system has an indifferent electrode on the lead located proximally to the active electrode. Programmable polarity systems can switch the indifferent electrodes in order to obtain either bipolar or unipolar pacing.

Since muscle twitching is provoked by a high strength electric field within the muscle, the majority of unipolar pacemakers use a partially insulated can in a manner which directs the electric field of the indifferent electrode toward the skin. A thin insulation layer covering the can is interrupted to leave a relatively small uninsulated area on one side of the can which serves as the indifferent electrode.

A body tissue stimulation apparatus with a warning device has been proposed in U.S. Pat. No. 4,140,131. An implantable pacemaker comprising a battery voltage level detector as well as a lead impedance level detector is disclosed. If the voltage level falls below a predetermined limit or the lead impedance changes so that it is outside a predetermined range, the warning device will be activated. The warning device includes a special output circuit which is isolated from the pacing output circuit and an auxiliary electrode (cathode). Bipolar warning stimulation of the muscle is performed through the auxiliary electrode and the indifferent electrode (pacemaker can). Different rates of the warning pulse train are used to indicate battery depletion and lead failure respectively. In the disclosed embodiment, the additional output circuit drains additional power from the battery. If the auxiliary electrode is surrounded by the indifferent electrode (as disclosed), it may be fixed on the pacemaker can. A consequence is that pacemaker can production is a more complex undertaking. Insulation and sealing between the auxiliary and indifferent electrodes as well as a more complex design of the pacemaker can are required.

It is also desirable to provide an alarm to a patient if failures other than battery and lead malfunction occur or if cardiac arrhythmias occur. It is not important that the patient be given enough information to diagnose the nature of the malfunction. It is much more desirable that the patient be able to differentiate between non hazardous malfunctions or alarms given merely for diagnostic purposes, and alarms for hazardous malfunctions. It is very important that the pacemaker include a reliable mode of back-up or safety pacing.

DISCLOSURE OF THE INVENTION

It is a principle object of the invention to provide a pacemaker which provokes the twitching of a pocket muscle adjacent to the implanted pacemaker in order to provide an alarm to the patient whenever a pacing system failure, a pacing disturbance or malfunction, or a cardiac arrhythmia is about to occur or has occurred.

It is a particular object of the invention to obtain muscle twitching without incorporating an additional output circuit for muscle stimulation within the pacemaker.

It is an additional object of the invention to provide two levels of patient alarm; a low-level alarm for warning about non-hazardous malfunctions and events of diagnostic importance, and an emergency level alarm for warning about hazardous failures and malfunctions.

It is a further object of this invention to enable the patient to temporarily deactivate the low-level alarm by means of an external device in order to avoid discomfort.

It is another object of the invention to provide a pacemaker wherein deactivation of the low level alarm does not affect operation of the high-level emergency alarm.

It is still another object of the invention to provide an auto-controllable cardiac pacemaker including circuitry for diagnoses of lead failure, electronic circuit failure, battery depletion and loss of capture.

It is yet another object of the invention to provide an auto-controllable pacemaker incorporating means for detection of pacing disturbances and cardiac arrhythmias, as well as event counters and memory for diagnostic purpose.

It is a further particular object of the invention to provide a pacemaker which can be programmed by and provide data to an external programmer, in order to determine which values of measured parameters and which events or quantity of events will activate the required type of alarm, as well as to enable test and to facilitate adjustment of alarm thresholds.

In accordance with a first aspect of the invention an apparatus for administering electrotherapy to the heart includes and alarm electrode having a small surface area which can serve as an indifferent electrode mounted on a non-conductive portion of the case of the apparatus such as the neck. The non-conductive portion of the case may be configured with a recess for receiving the alarm electrode. The recess and the alarm electrode may be sized and shaped relative to one another so that the alarm electrode does not extend from the recess. The alarm electrode may be conical in shape and disposed within the recess so that the apex points outwardly away from the case.

In accordance with a further aspect of the invention the apparatus includes a switch which disconnects an output of a pulse forming circuit within the apparatus from electrical contact with a conductive portion of the case and connects the output of the pulse forming circuit to the alarm electrode when an internal alarm means or detector senses a change in the nature of the electrotherapy. When the apparatus is disposed so that the alarm electrode contacts a pocket muscle, the resulting increase in current density causes the muscle to twitch.

An energy control means may be provided for changing the energy of the electrotherapy pulses in response to an output from the alarm means. The energy may be increased to a maximum value when the alarm means senses a change in the nature of the electrotherapy which may be hazardous to the patient thus providing a more intense twitching of the muscle.

In accordance with an additional aspect of the invention, a back-up pacing circuit is provided so that when the alarm means detects a condition indicative of selected changes in the nature of the electrotherapy supplied by the apparatus, back-up pacing pulses are provided.

BRIEF DESCRIPTION OF THE DRAWINGS

Further objects, features and advantages of the invention will become apparent upon consideration of the following detailed description in conjunction with the drawings, in which:

FIG. 2A, FIG. 2B and FIG. 2C are cross-sectional views of preferred shapes of the alarm electrode and a portion of the plastic neck of the pacemaker in accordance with the invention;

FIG. 5A to FIG. 5F are flow charts illustrating the manner in which the microprocessor circuit of FIG. 3 polls the various functions of the pacemaker in accordance with the invention.

DETAILED DESCRIPTION OF THE PREFERRED EMBODIMENTS

While the present invention is described with respect to an autocontrollable pacemaker, it will be understood that it may be used in other devices for administering electrotherapy to the heart, such as other types of pacemakers, implantable cardioveters and defibrillators.

Figure 1:
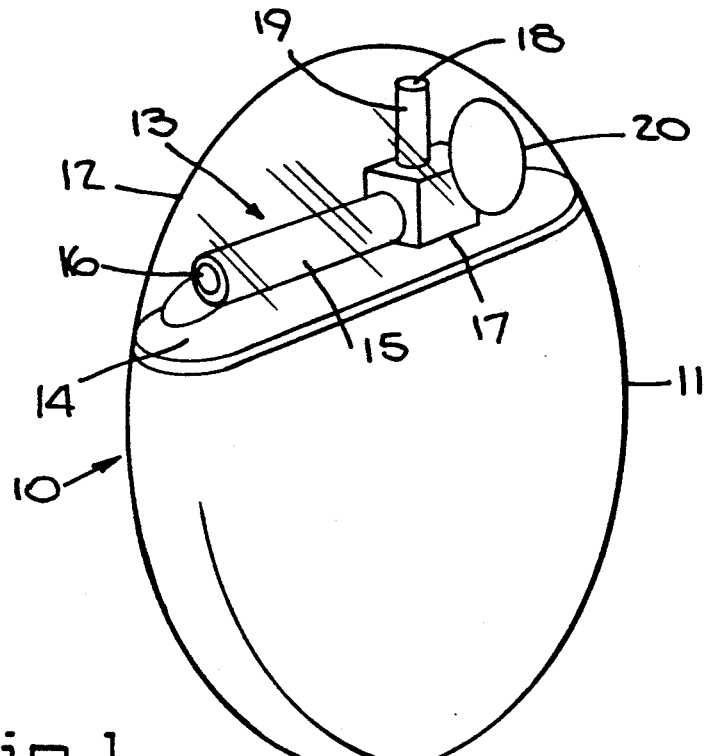
FIG. 1 is a perspective view of a pacemaker case constructed in accordance with the invention.

Referring to FIG. 1, there is shown a pacemaker case 10 of a unipolar implantable pacemaker. The case includes two major components: a metal can 11 and a plastic neck 12. In all unipolar pacemakers the metal can is normally connected to the positive pole of the pacing output circuit and therefore it is also the indifferent electrode (anode) of the unipolar pacing system. The battery and the electronic circuits (not shown), are hermetically sealed within can 11. A connector system, show generally as 13, for connecting a lead to the pacemaker is within plastic neck 12 and is affixed to the top planar surface 14 of can 11. Since the neck is made of transparent material, connector system 13 is visible. Connector system 13 comprises a hollow cylinder 15 for receiving a lead terminal (not shown) inserted through an aperture 16 in neck 12. A rectangular connection block 17 receives a terminal pin (not shown) of the lead. The terminal pin is secured within block 17 by a set screw (not shown) which, when rotated by a screwdriver (not shown) inserted through an aperture 18 in neck 12, travels longitudinally along a cylindrical set screw housing 19.

In accordance with the invention, an alarm electrode 20 is mounted and fixed on plastic neck 12. Alarm electrode 20 is a small, conductive electrode having an impedance within a predetermined range of impedances. In order to decrease impedance and polarization, the alarm electrode may have a porous surface.

Referring to FIG. 2A, FIG. 2B and FIG. 2C, three possible geometric shapes of the alarm electrode are illustrated. In FIG. 2A, alarm electrode 20 is of a button or dome shape with a cylindrical rear portion embedded in an annular recess in pacemaker neck 12 (FIG. 1). Wire 22, affixed to a rear planar surface of electrode 20, is used for electrical connection of the electrode 20 to the pacemaker circuits (not shown in FIG. 2A).

In a further embodiment, as disclosed in FIG. 2B, an alarm electrode 23 is formed in the shape of a disc or plate, and is also partially embedded in a circular recess in pacemaker neck 24. There is also a connecting wire 25, affixed to a rear planar surface of electrode 23, for electrical connection to the pacemaker circuits.

In the embodiment of FIG. 2C, the alarm electrode 26 is needle or cone shaped. Pacemaker neck 27 is formed with a relatively deep and wide recess 28 from which electrode 26 does not protrude. In other words, electrode 26 is completely embedded within the contours of the neck so as to form a free space for tissue ingrowth and to prevent the needle tip from causing mechanical trauma to the surrounding tissue. The rear portion of electrode 26, which has a planar surface to which a connecting wire 29 is attached, is embedded in a second recess in neck 27 extending from the bottom of recess 28. In practice neck 27 may be molded with electrode 26 in place.

Figure 3:
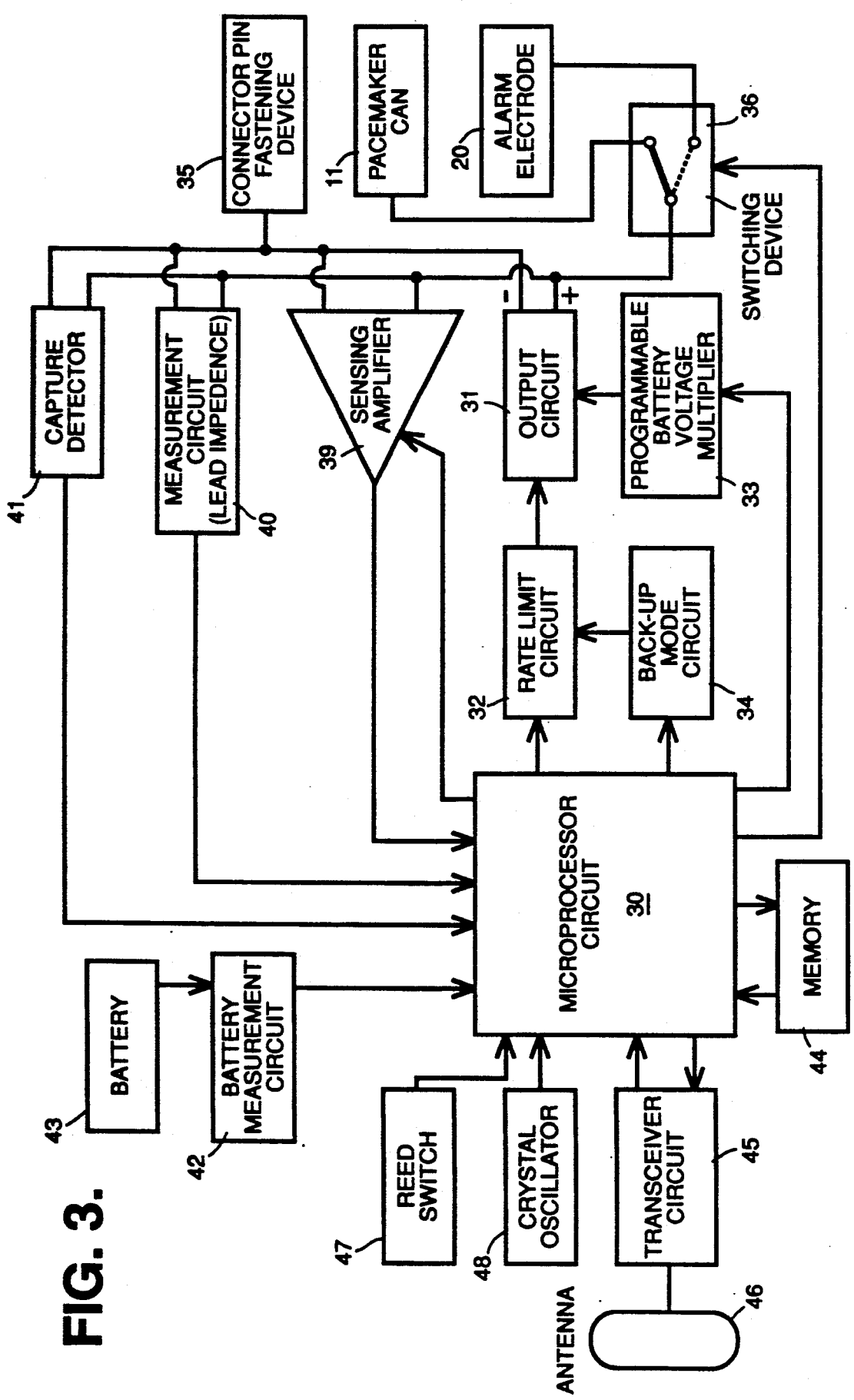
FIG. 3 is a functional block-diagram of a microprocessor-controlled pacemaker with switching devices for the alarm-electrode which is connected in-circuit with the heart.

The invention may be used in the unipolar single chamber autocontrollable pacemaker of FIG. 3 which is controlled by means of a microprocessor circuit 30 which provides logic and control functions, including digital processing, storage and timing necessary for operation of the invention. Microprocessor circuit 30 includes a microprocessor and associated components for interfacing the microprocessor to the other circuitry of the pacemaker.

The pacing output signal of circuit 30 is provided to an output circuit 31 through a rate limit circuit 32. Rate limit circuit 32 prevents excessively rapid pacing, thus protecting the patient against high rate failures in circuit 30. Output circuit 31 is basically a pulse amplifier powered by a programmable battery voltage multiplier 33, thereby permitting the magnitude of the output pulses to be varied under the control of microprocessor circuit 30. In order to ensure the maintenance of essential functions should certain components fail, a back-up mode circuit 34 is included.

The negative pole of output circuit 31 is connected to an electrical contact 35 associated with connector system 13, which accepts a lead (not shown) having an active electrode (cathode) within the heart (not shown). The positive pole of output circuit 31 is connected to a switching device 36 which is controlled by microprocessor circuit 30. Switching device 36 connects the positive pole of output circuit 31 either to pacemaker can 11 or to the alarm electrode, which may be any one of those illustrated in FIG. 2A, FIG. 2B or FIG. 2C; but is designated as electrode 20. The switch position shown in FIG. 3 illustrates the normal connection for unipolar pacing. While a single pole double throw switch is used to illustrate the principle, in practice two single pole single throw semiconductor switches may be used, with the two switches always being in opposite states.

The input terminals of a sensing amplifier 39 are electrically connected by appropriate leads to the active electrode by way of electrical contact 35 and to one of the indifferent electrodes (by way of switch 36), respectively. Microprocessor circuit 30 processes signals from the sensing amplifier 39 so as to distinguish between cardiac signals and extraneous electrical interference signals and to detect cardiac arrhythmias. Microprocessor circuit 30 controls the gain of the amplifier 39 in order to obtain programmable sensitivity and also stores detected events in data registers in a memory 44. A measurement circuit 40 measures lead impedance upon receiving an appropriate command from microprocessor circuit 30 which then stores a digital representation of the numerical value of lead impedance in a data register in memory 44.

The output signal of a capture detector 41 having inputs connected in parallel with those of sensing amplifier 39 indicates to microprocessor circuit 30 whether capture of the heart by the output pulses of output circuit 31 has occurred.

Upon receipt of an appropriate command from microprocessor circuit 30, a battery measurement circuit 42 measures the battery voltage, the internal battery impedance and the battery drain current. A possible implementation for a pacemaker battery impedance test circuit is disclosed in U.S. Pat. No. 4,606,350 to Frost, assigned to the same assignee as that of the present invention. Digital representations of the numerical values are stored in data registers in memory 44. A battery 43 serves as a power source for all circuits. Memory 44 is controlled by microprocessor 30 and is used for the temporary storage of data for diagnostic and telemetric purposes. A transceiver circuit 45 and an antenna 46 provide bi-directional communication between an external programmer (not shown) and microprocessor circuit 30. A reed switch 47 permits microprocessor circuit 30 to sense the application of an external magnet.

Precision timing signals are supplied to microprocessor circuit 30 by a crystal oscillator 48.

Figure 4:
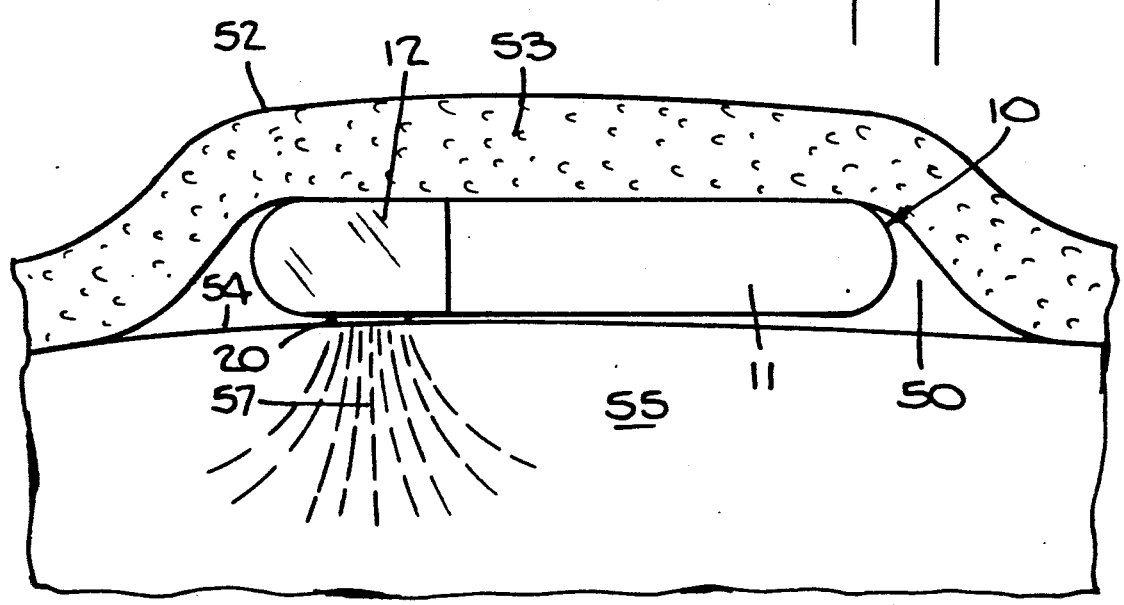
FIG. 4 is a cross-sectional view of an implanted pacemaker having an alarm electrode according to FIG. 2B implanted in tissues within the human body.

Referring to FIG. 4, the pacemaker is implanted in the human body within a surgically prepared pocket 50 under the skin 52 and the subcutaneous tissue 53. It is positioned on the aponeurosis 54 of a muscle 55, so as to obtain contact between the alarm electrode 20 and the aponeurosis 54. The illustrated tissue cross-section represents the pacemaker pocket in the acute post-implantation period.

After some time, fibrous tissue surrounds the pacemaker case and both can 11 and alarm electrode 20 maintain electrical contact with the surrounding tissue through a fibrous membrane (not shown).

Normally, during unipolar pacing, the large-area can 11 serves as the indifferent electrode and produces a widespread electric field having a relatively low anodal current density and which usually cannot provoke muscle stimulation in the normal range of low energy output pulses. Whenever an alarm condition is detected, switch 36 (FIG. 3) switches from the position in which can 11 serves as the indifferent electrode to the position in which alarm electrode 20 serves as the indifferent electrode. Since the pacemaker is simultaneously programmed to high energy output, a high strength electric field is produced with lines of force 57 which emanate from the alarm electrode 20. Thus, there is a high anodal current density which evokes an action potential within the muscle 55 in the vicinity of electrode 20.

FIGS. 5A to 5F, taken together, are a flowchart illustrating the logic control program of microprocessor circuit 30 (FIG. 3). There are two alarm mode routines: the emergency alarm of FIG. 5A and the low level alarm of FIG. 5B. Connection entry blocks are designated by 60 for emergency alarm and by 69 for low level alarm. The alarm modes of pacing can be tested and adjusted by an external programmer. The low level and the emergency alarm can be switched on and off for test purposes to verify that the patient feels the muscle twitching and to evaluate the alarm mode of pacing.

The sequence of operations in the emergency alarm mode starts with a change to the VVT mode of pacing at 61. The pacemaker is programmed to the nominal pacing frequency at 62 and to the highest possible output at 63. After the alarm electrode has been switched on at 64, the programmed indifferent electrode is switched off at 65. Whenever the emergency alarm is activated, the pacemaker is programmed to the back-up mode at 66 which abandons microprocessor control at 67 and ends software program execution at 68.

In the alarm adjustment mode of FIG. 5B, the special conditions of a low level alarm are defined: the muscle twitching threshold is determined and a suprathreshold output value for low level alarms can be stored at 70. Furthermore, other parameters are defined and stored at 70. Whenever the low level alarm is activated, the stored values are recalled from memory 44 (FIG. 3) at 71 and the pacemaker is automatically reprogrammed to the predetermined suprathreshold output at 72. Other parameters are also programmed to the predetermined stored values at 72. The indifferent electrodes are switched at 73 and 74 to produce the muscle twitching by changing the state of switching device 36 (FIG. 3). In order to avoid patient discomfort, the alarm may be switched off by the application of an external magnet. Therefore reed switch 47 (FIG. 3) is monitored at 75 and when it is closed, the indifferent electrodes will be switched at 76 and 77 thereby ending the low level alarm mode at 78.

After the alarm modes have been defined and programmed, the alarm criteria can be selected by the external programmer. The low level alarm criteria can be stored independently of the emergency alarm criteria. The alarm criteria include numerical values for parameters which are stored and compared with the measured values of corresponding parameters. The upper and/or lower limits of measured parameters must be programmed in order to define which values of measured parameters will activate the low level alarm or the emergency alarm.

Figure 5C:
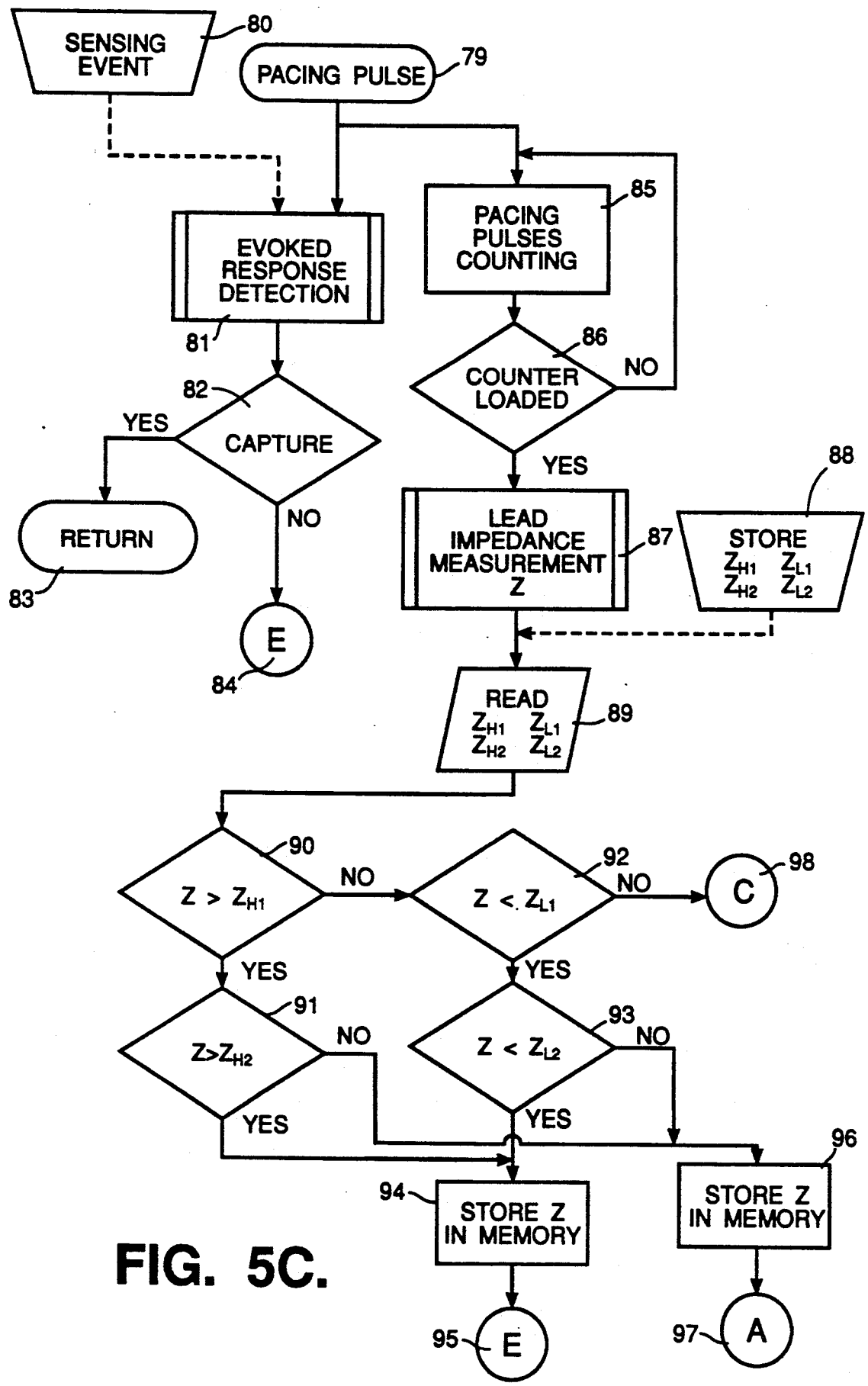

Referring to FIG. 5C, the pacemaker monitors the capture of every pacing pulse. Each pacemaker pulse is monitored at 79 and the evoked response is sensed at 80. For each pulse, the evoked response detection subroutine at 81 determines if an evoked response occurred. If capture is maintained, as determined at 82, this sequence is terminated at 83 until the next pacing pulse occurs. If loss of capture is detected at 82, the emergency alarm will be activated at 84, as branching to the routine of FIG. 5A occurs.

Periodically, the lead must be checked in order to avoid the sudden loss of capture caused by lead conductor or lead insulation failure. Therefore the pacing pulses are counted at 85 and 86 and whenever the number of pulses reaches a value equal to the maximum count of a counter, the lead impedance measurement subroutine at 87 is initiated. The upper and lower limits of the lead impedance Z are programmed twice; once for low level alarm and again for emergency alarm. All the values are stored in memory 44 (FIG. 3) at 88. After the lead impedance measuring procedure has been executed, microprocessor circuit 30 reads the first high (ZH1), first low (ZL1), second high (ZH2) and second low (ZL2) limit of lead impedance from memory 44 at 89. The measured impedance is then compared with the predetermined limits to activate the low level alarm if the lead impedance increases or decreases so that it is outside a range defined by the first programmed limits, and to activate the emergency alarm if the lead impedance changes outside a second, broader range defined by a second set of programmed limits.

First, the microprocessor checks if Z is greater than the first high limit at 90. If it is greater, then the microprocessor checks if Z is greater than the second high limit at 91. If the answer is yes, the microprocessor stores the measured value Z in memory at 94 for later retrieval by the programmer and starts the sequence of emergency alarm programming at 95. If Z has a value between two high limits ZH1 and ZH2, it also will be stored at 96 and the sequence of low level alarm programming will be initiated at 97. If Z is not greater than ZH1, it will be compared with the first low limit at 92. If it is smaller than ZL1, it will be compared with the second low limit 93. If it is smaller than ZL2, it will be stored at 94 and emergency alarm programming will start at 95, due to branching to the routine of FIG. 5A. If Z has a value between low limits ZL1 and ZL2, it will be stored in memory at 96 and the low level alarm programming will be initiated at 97, due to branching to the routine of FIG. 5B.

Figure 5D:
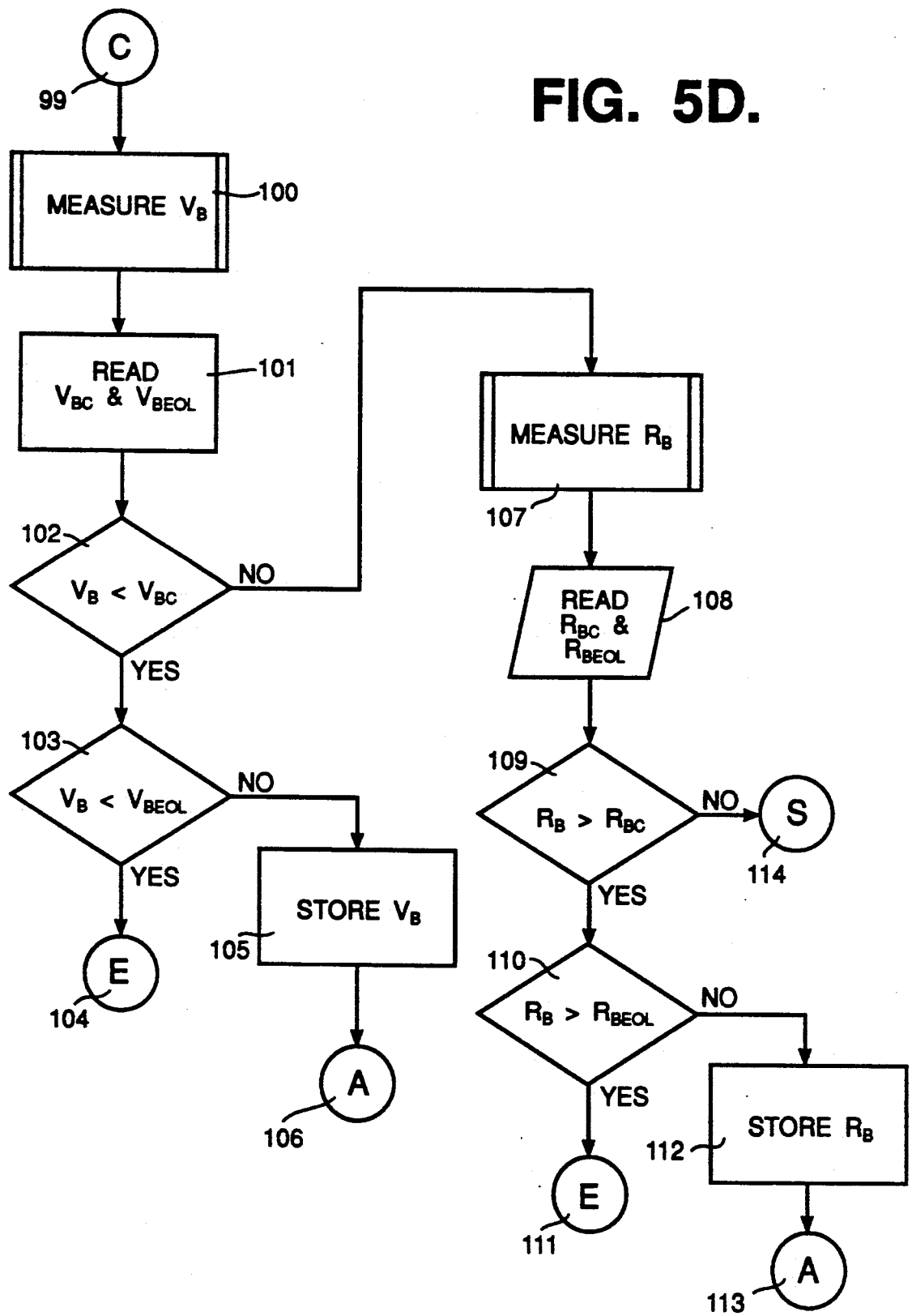

If Z is not smaller than ZL1, the logic sequence of autocontrol will continue at 98. Referring to FIG. 5D, the battery control sequence will be initiated at 99. The battery voltage and the internal battery impedance alarm limits are preferably predetermined by the pacemaker manufacturer and stored in a ROM portion of memory 44. These values should not be accessible to change by a programmer. After the battery voltage Vb is measured at 100, the first, critical battery voltage limit Vbc and the end of life battery voltage Vbeol are read from the ROM memory portion of memory at 101. First, the measured voltage Vb is compared to the critical voltage Vbc. If Vb is smaller than Vbc, Vb is compared to Vbeol at 103. If Vb is smaller than Vbeol, the emergency alarm programming will be initiated at 104. Branching to the routine of FIG. 5A occurs. If Vb has a value between the critical voltage and the end of life voltage, its value is stored at 105 for later retrieval and low level alarm programming initiated at 106 due to branching to the routine of FIG. 5B. If the battery voltage is not lower than the critical value, the measurement of internal battery impedance Rb will be initiated at 107.

The critical battery impedance Rbc and the end of life battery impedance Rbeol are read from the ROM portion of memory and the measured value Rb is compared first with Rbc at 109. If Rb is greater than Rbc, Rb will be compared with Rbeol at 110. If Rb is greater than Rbeol, emergency alarm programming will be started at 111 due to branching to the routine of FIG. 5A. If Rb has a value between the critical impedance and the end of life battery impedance, its value will be stored at 112 and branching to the low level alarm routine of FIG. 5B will occur at 113.

Figure 5E:
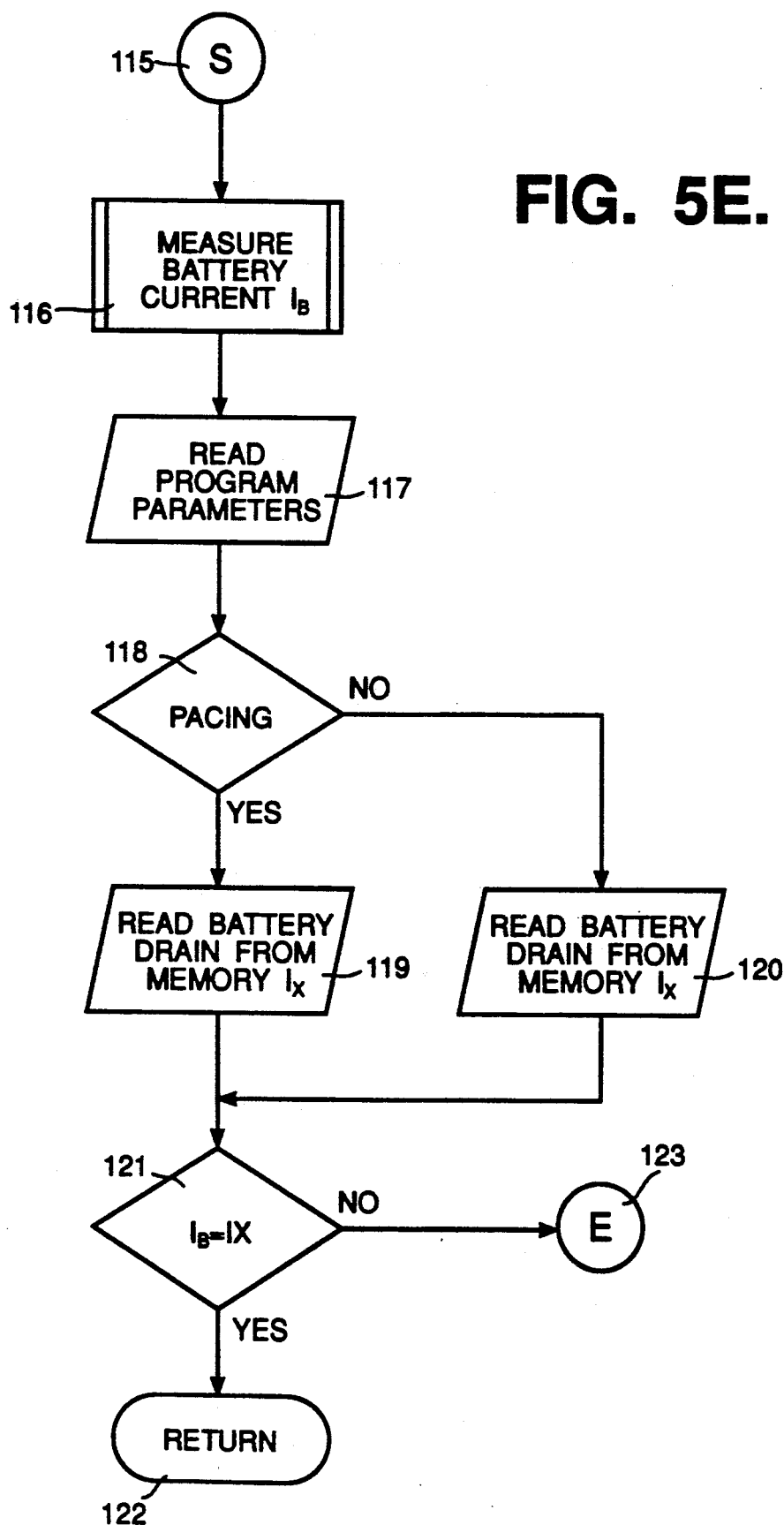

If Rb is not greater than Rbc, a sequence of battery drain current monitoring will be initiated at 114 by transfer to FIG. 5E at 115. In this special autocontrol function, microprocessor circuit 30 continuously monitors battery drain current in relation to pacemaker function. Normally, a sudden change of drain current occurs during output programming as well as during the rhythm change from sensing to pacing and vice versa. Some other sudden changes in power consumption may occur according to the specifics of the electronic design of various electrotherapy apparatus. If a change of battery drain current occurs which is not related to the normal function of the pacemaker electronic circuits, there is a suspected failure of these circuits. As a result of the design process of the relevant electronic circuits, the current consumption is known for every possible combination of programmed parameters as well as for every possible rhythm (sensing, various modes of pacing, etc). Therefore a table of expected battery drain currents for every possible pacemaker function is stored in the memory.

The following flowchart sequence is an example of the sequence of events for a VVI pacemaker. The sequence is initiated with a subroutine at 116 for measurement of battery drain current Ib. The programmed parameters are read from the program register at 117 and the microprocessor checks whether the rhythm is pacing or sensing at 118. If it is pacing, the microprocessor circuit reads from memory at 119 the expected battery drain current Ix corresponding to the programmed parameters and pacing. If it is sensing, the microprocessor reads from memory at 120 the expected battery drain current Ix corresponding to the programmed parameters and sensing. If the measured current Ib and the expected current Ix are equal (within normal tolerance limits) at 121, the sequence ends at 122 until it is again initiated. If the compared currents are not equal at 122, the emergency alarm programming sequence will be initiated at 123 due to branching to the routine of FIG. 5A.

Figure 5F:
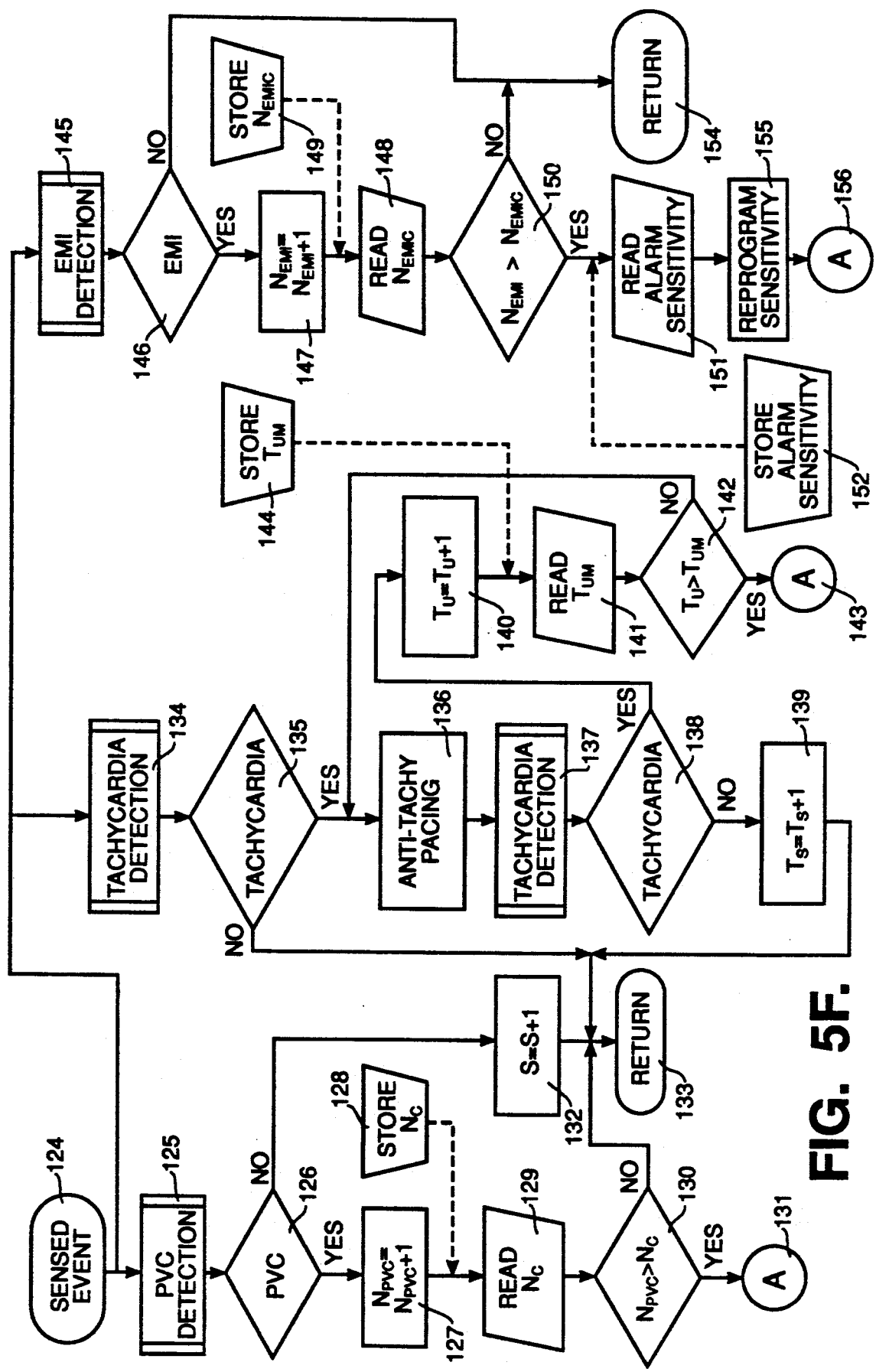

Referring to FIG. 5F, the diagnostic alarm criteria are programmable in the same manner as the autocontrol criteria based on limits associated with particular events, such as premature ventricular contractions (PVCs), tachycardias, and electromagnetic interference (EMI). Appropriate alarm limits are stored. Whenever the alarm is activated, the measured number of events is automatically stored for later retrieval by the programmer. Every sensed event at 124 starts the subroutine for PVC detection at 125. If the PVC is detected at 126, the PVC counter will be incremented at 127. The microprocessor reads the critical number Nc of PVCs from memory at 129 where it was previously stored by the programmer at 128. If the number of detected PVCs Npvc exceeds the critical number Nc at 130, the low level alarm will be activated at 131 due to branching to the routine of FIG. 5B. If Npvc is smaller than Nc, the sequence is terminated at 133 until the next sensing event. If there are no PVCs at 126, the spontaneous rhythm counter is incremented at 132, and the sequence is terminated at 133 until the next sensed event.

If the pacemaker includes an antitachycardia function, the sensed events at 124 initiate a tachycardia detection algorithm at 134. If tachycardia is not detected at 135, the sequence is terminated at 133. If tachycardia is detected at 135, a mode of antitachycardia pacing is initiated at 136. The tachycardia detection algorithm at 137 is initiated again in order to check, at 138, whether the tachycardia has been terminated. If there is no tachycardia, the successful terminations counter Ts is incremented at 139 and the sequence ends at 133. If tachycardia persists, the unsuccessful terminations counter Tu is incremented at 140. Microprocessor circuit 30 reads, at 141, the maximum number of unsuccessful terminations Tum, which was previously programmed at 144, and compares this number with the number of unsuccessful terminations Tu at 142. If the number of unsuccessful terminations Tu exceeds the prescribed maximum Tum, the low level alarm sequence will be initiated at 143 by branching to the routine of FIG. 5B. If Tu is lower than Tum, antitachycardia pacing will start again at 136.

Sensed events at 124 also may be electromagnetic interference (EMI) and therefore some algorithm, which may be any one of several well known methods of EMI detection, is utilized at 145. If there is no EMI at 146 the program ends at 154. However, if the microprocessor recognizes EMI at 146, an EMI events counter will be incremented at 147. Microprocessor circuit 30 will read, at 148, the critical number of EMI events Nemic, previously programmed at 149, and will compare it to the number of detected EMI events Nemi at 150. If the number of EMI events Nemi is smaller than the critical value Nemic, the sequence will end at 154. If Nemi is greater than Nemic, the microprocessor will read, at 151, the alarm sensitivity previously programmed at 152 and reprogram the pacemaker to this sensitivity at 155. The low level alarm sequence will be initiated at 156 due to branching to the routine of FIG. 5B.

While the invention has been described with respect to a pacemaker that performs unipolar pacing, the invention is equally applicable to a pacemaker that performs bipolar pacing. To provide either an emergency alarm or a low level alarm, it is necessary for the pacemaker to switch from the bipolar mode of pacing to unipolar pacing. The indifferent electrode is first switched from the ring electrode to the pacemaker case. There are pacemakers on the market which can be controlled to perform this function. Then, as described above, the indifferent electrode is again switched. Instead of the large surface area pacemaker can, the smaller surface area alarm electrode is used. Alternatively, it is possible for switching to occur directly from the ring electrode to the alarm electrode.

Although the invention has been described with reference to particular embodiments, it is to be understood that these embodiments are merely illustrative of the application of the principles of the invention. Numerous modifications may be made therein and other arrangements may be devised without departing from the spirit and scope of the invention.

I claim:

1. In an implantable apparatus for administering electrotherapy pulses to the heart, said apparatus having a power source and circuitry powered by said power source, said circuitry including a pulse forming circuit for providing said pulses and an alarm means for providing an output indicative of selected, predetermined changes in one of the manner in which said apparatus provides electrotherapy, the condition of said apparatus, and electrical activity of the heart, said apparatus having a case with a first portion formed of a conductive material and a second portion formed of an insulating material, the improvement comprising:

an alarm electrode mounted externally of said second portion, said alarm electrode being substantially smaller in dimensions than said case; and switch means responsive to said output from said alarm means for electrically connecting the pulse output of said pulse forming circuit to said alarm electrode.

2. The apparatus of claim 1, further comprising a lead to the heart, said lead having a second electrode, wherein said alarm electrode is of a sufficiently small surface area, so that when said apparatus is disposed adjacent a muscle and said switch means has electrically connected said output of said pulse forming circuit to said alarm electrode, said pulses produce a sufficiently large current density in said muscle so that said muscle is caused to twitch.

3. The apparatus, of claim 2, wherein said second electrode is for conducting said electrical pulses directly to the heart, said output of said pulse forming circuit, said lead to the heart, said second electrode, the heart and said alarm electrode being electrically in series.

4. The apparatus of claim 1, further comprising a lead to the heart, said lead having a second electrode, said second electrode being for conducting said electrical pulses directly to the heart, said output of said pulse forming circuit, said lead to the heart, said second electrode, the heart and said alarm electrode being electrically in series.

5. The apparatus of claim 1, further comprising energy control means responsive to said output from said alarm means, said energy control means being for controlling the energy of said electrotherapy pulses.

6. The apparatus of claim 5, wherein said alarm means varies said output to provide an output signal indicative of a class of severe insufficiencies in said electrotherapy, and wherein said energy control means is responsive to said output signal to control said pulse circuit to increase energy of said electrotherapy pulses.

7. The apparatus of claim 6, wherein said energy control means includes a programmable voltage multiplier for supplying power for operation of said pulse forming circuit.

8. The apparatus of claim 7, wherein said energy control means further comprises a microprocessor, said microprocessor having outputs for programming said programmable voltage multiplier.

9. The apparatus of claim 5, wherein said energy control means includes a programmable voltage multiplier for supplying power for operation of said pulse forming circuit.

10. The apparatus of claim 9, wherein said energy control means further comprises a microprocessor, said microprocessor having outputs for programming said programmable voltage multiplier.

11. The apparatus of claim 1, further comprising back-up pacing means responsive to said output of said alarm means for placing said apparatus in a back-up pacing mode in the event of predetermined changes in one of the manner in which said apparatus provides said electrotherapy and the condition of said apparatus.

12. The apparatus of claim 1, wherein said second portion of said case has a recess for receiving said alarm electrode, said recess is sized and shaped so that a first portion of said alarm electrode is received in said recess and a second portion of said alarm electrode extends from said recess.

13. The apparatus of claim 12, wherein said second portion of said alarm electrode ,is dome shaped.

14. The apparatus of claim 12, wherein said second portion of said alarm electrode is in the shape of a disc.

15. The apparatus of claim 1, wherein said second portion of said case has a recess, and said recess and said alarm electrode are sized and shaped relative to one another so that said alarm electrode does not protrude outside said recess.

16. The apparatus of claim 15, wherein said alarm electrode is conical in shape and has an apex pointing away from said case.

17. The apparatus of claim 15, wherein said recess is interconnected to a second recess, said second recess being for receiving a first portion of said alarm electrode, said second recess and said first portion of said alarm electrode being sized and shaped so that said alarm electrode is fixedly attached to said second portion of said case.

18. The apparatus of claim 1, wherein said second portion of case forms a neck of said apparatus.

19. In an implantable apparatus for administering electrotherapy pulses to the heart, said apparatus having a power source and circuitry powered by said power source, said circuitry including a pulse forming circuit for providing said pulses and an alarm means for providing an output indicative of a selected, predetermined change in the manner in which said apparatus provides electrotherapy, said apparatus having a case for housing components thereof, the improvement comprising:
  muscle stimulation means for stimulating a muscle in contact therewith, said muscle stimulation means being electrically connected to an output of said pulse circuit;
  detector means for detecting when said change in said manner in which said apparatus provides said electrotherapy constitutes a severe insufficiency and for providing an insufficiency signal; and
  energy control means responsive to said insufficiency signal, said energy control means being for controlling said pulse circuit to increase energy of said electrotherapy pulses.

20. The apparatus of claim 19, wherein said energy control means includes a programmable voltage multiplier for supplying power for operation of said pulse forming circuit.

21. The apparatus of claim 20, wherein said detector means comprises a microprocessor, said microprocessor having outputs for programming said programmable voltage multiplier.

22. The apparatus of claim 19, wherein said stimulation means comprises an electrode mounted on an external surface of said case.

23. The apparatus of claim 22, wherein said case has a portion formed of an insulator and said electrode is on said portion.

24. The apparatus of claim 23, wherein said portion of said case has a recess for receiving said electrode, said recess is sized and shaped so that a first portion of said electrode is received in said recess and a second portion of said electrode extends from said recess.

25. The apparatus of claim 24, wherein said portion of said second electrode is dome shaped.

26. The apparatus of claim 24, wherein said portion of said second electrode is in the shape of a disc.

27. The apparatus of claim 23, wherein said portion of said case has a recess, and said recess and said electrode are sized and shaped relative to one another so that said electrode does not protrude outside said recess.

28. The apparatus of claim 27 wherein said electrode is conical in shape, and an apex of said electrode points away from said case.

29. The apparatus of claim 27, wherein said recess is interconnected to a second recess, said second recess being for receiving a first portion of said electrode, said second recess and said first portion of said electrode being sized and shaped so that said electrode is fixedly attached to said portion of said case.

30. The apparatus of claim 19, further comprising back-up pacing means responsive to said output of said detector means for placing said apparatus in back-up pacing mode in the event of selected changes in the manner in which said apparatus provides electrotherapy.

31. In an apparatus for administering electrotherapy pulses to the heart, the apparatus comprising an alarm signal generator, a conductive case and a non-conductive neck, said conductive case constituting an electrode for producing a low current density field, the improvement comprising an alarm electrode connected to said alarm signal generator for producing a high current density field, said alarm electrode being mounted on an external surface of said neck and being positioned to contact a muscle adjacent thereto so as to provide an alarm signal to a user when activated.

32. The apparatus of claim 31, wherein said neck is configured with a recess for receiving said alarm electrode, said recess and said electrode being sized and shaped relative to one another so that said alarm electrode does not protrude outside of said recess.

33. The apparatus of claim 32, wherein said alarm electrode is shaped in the form of a cone, the cone being positioned in said recess so that an apex of said cone points outwardly away from said neck of said apparatus.

34. An apparatus for administering electrotherapy pulses to the heart, comprising:
  pulsing means for delivering said pulses to the heart;
  low level alarm means for providing an alarm indicative of a minor malfunction in the providing of said electrotherapy pulses, said low level alarm means providing electrical pulses to a user's muscle at an energy level which causes twitching but not severe contractions of the muscle so that the user is informed that a minor malfunction has occurred; and
  emergency alarm means for providing an alarm indicative of a major malfunction in the providing of said electrotherapy pulses, said emergency alarm means providing electrical pulses to the user's muscle at an energy level which causes severe contractions of the muscle so that both the user and any other observer present are informed that a major malfunction has occurred.

35. The apparatus of claim 19 further comprising:
  evaluating means for evaluating the providing of malfunction or a major malfunction;
  switch means responsive to said evaluating means for switching to said low level alarm means when a minor malfunction occurs and said emergency alarm means when a major malfunction occurs.

36. The apparatus of claim 35 further comprising pacing means for pacing the heart when selected malfunctions occur.

37. The apparatus of claim 36 further comprising:
  means for switching to VVT pacing mode when a major malfunction occurs.

38. The apparatus of claim 36 further comprising:
  means for selecting a predetermined frequency at which said pacing means operates.

39. The apparatus of claim 36 further comprising means for increasing energy of said pacing means.

40. The apparatus of claim 36 wherein said energy increasing means comprises:
  first energy level setting means for setting energy for a low level alarm; and second energy level setting means for setting energy for an emergency alarm.

41. The apparatus of claim 34 further comprising patient operated means for disabling operation of said low level means while permitting operation of said emergency alarm means.

42. The apparatus of claim 34, further comprising
sensing means for sensing values associated with at least one of lead impedance, battery voltage, battery impedance, battery current, premature ventricular contractions, electromagnetic interference, tachycardia, and unsuccessful reversion of tachycardia;

parameters storage means for storing parameters indicative of a low level alarm condition and an emergency alarm condition for the at least one parameter sensed; and comparison means for comparing sensed values to the stored parameters to determine whether a low level alarm condition or an emergency alarm condition exists.

43. The apparatus of claim 42, further comprising:
means for sensing loss of capture of the heart, and
means for providing an emergency alarm when loss of capture occurs.

* * * * *